United States Patent
Yun et al.

(10) Patent No.: US 10,898,128 B2
(45) Date of Patent: Jan. 26, 2021

(54) ENHANCING REPRODUCTIVE CAPACITY BY PARADOXICAL THERAPY

(71) Applicant: Palo Alto Investors, Palo Alto, CA (US)

(72) Inventors: Anthony Joonkyoo Yun, Menlo Park, CA (US); Conrad Minkyoo Yun, San Mateo, CA (US); Kimberly A. Bazar, Palo Alto, CA (US)

(73) Assignee: Palo Alto Investors, Palo Alto, CA (US)

( * ) Notice: Subject to any disclaimer, the term of this patent is extended or adjusted under 35 U.S.C. 154(b) by 344 days.

(21) Appl. No.: 15/976,421

(22) Filed: May 10, 2018

(65) Prior Publication Data

US 2018/0344236 A1  Dec. 6, 2018

Related U.S. Application Data

(60) Provisional application No. 62/513,301, filed on May 31, 2017.

(51) Int. Cl.

| | | |
|---|---|---|
| A61B 5/00 | (2006.01) | |
| A61B 5/0205 | (2006.01) | |
| A61B 5/11 | (2006.01) | |
| G16H 20/10 | (2018.01) | |
| G16H 20/90 | (2018.01) | |
| G16H 20/30 | (2018.01) | |
| A61B 5/0476 | (2006.01) | |
| G16H 20/70 | (2018.01) | |

(52) U.S. Cl.
CPC .......... *A61B 5/4306* (2013.01); *A61B 5/0205* (2013.01); *A61B 5/1118* (2013.01); *A61B 5/4318* (2013.01); *A61B 5/4848* (2013.01); *A61B 5/4854* (2013.01); *A61B 5/4884* (2013.01); *A61B 5/0476* (2013.01); *A61B 5/4815* (2013.01); *G16H 20/10* (2018.01); *G16H 20/30* (2018.01); *G16H 20/70* (2018.01); *G16H 20/90* (2018.01)

(58) Field of Classification Search
CPC ..... A61B 17/42; A61B 17/425; A61B 17/435; A61B 34/10; A61B 2090/378
USPC .......................................................... 600/33
See application file for complete search history.

(56) References Cited

U.S. PATENT DOCUMENTS

| | | | | |
|---|---|---|---|---|
| 3,499,445 A | * | 3/1970 | Reed .................... | A61K 9/0024 604/500 |
| 2010/0160125 A1 | * | 6/2010 | Strong .................. | A63B 26/00 482/121 |
| 2014/0094421 A1 | * | 4/2014 | Sepahvand ........ | A61K 31/7034 514/25 |

FOREIGN PATENT DOCUMENTS

WO    WO2006044694 A2    4/2006

OTHER PUBLICATIONS

Farrow et al., Prolonged use of oral contraception before a planned pregnancy is associated with a decreased risk of delayed conception, Human Reproduction vol. 17, No. 10 pp. 2754-2761, 2002.

* cited by examiner

*Primary Examiner* — Samuel G Gilbert
(74) *Attorney, Agent, or Firm* — Peter W. Schroen; Bret E. Field; Bozicevic, Field & Francis LLP

(57) ABSTRACT

Methods of enhancing reproductive capacity in a female subject are provided. Aspects of the methods include inducing infertility in the subject in a manner effective to cause the subject to mount a compensatory response and thereby enhance reproductive capacity in the subject. Systems and kits useful in practicing the methods of the present disclosure are also provided.

16 Claims, No Drawings

ENHANCING REPRODUCTIVE CAPACITY BY PARADOXICAL THERAPY

CROSS-REFERENCE TO RELATED APPLICATIONS

Pursuant to 35 U.S.C. § 119 (e), this application claims priority to the filing date of U.S. Provisional Patent Application Ser. No. 62/513,301 filed May 31, 2017; the disclosure of which application is herein incorporated by reference.

INTRODUCTION

In 2010, an estimated 48.5 million couples worldwide were unable to have a child after five years of trying (See Mascarenhas et al., PLoS Med. 2012; 9(12):e1001356). Global infertility prevalence rates are difficult to determine, due to the presence of both male and female factors which complicate making any estimate which specifically addressed the female contribution to a couple's infertility. However, studies have shown that more women in developed countries, the United States included, are waiting until later in life to start having children. In 2013, the U.S. saw a record high average age of 26 years old for women having their first child, an increase of 3.3 years since 1980 (Marin et al., National Vital Statistics Report. (2015) 64(1):1-66). The average age of first-time mothers is increasing because more women are waiting until their 30s and 40s to start having kids and fewer women are having their first children in their teens and 20s. Fertility treatments have facilitated this trend making it easier in some cases, and possible in others, for women to have children later in life.

Roughly 1.3 million patients receive infertility advice or treatment each year in the U.S. The emotional effects of infertility, whether a result of a medical condition preventing pregnancy or decreased fertility due to advanced age, negatively impact many relationships and marriages. One study of 200 couples seen consecutively at a fertility clinic, for example, found that half of the women and 15% of the men said that infertility was the most upsetting experience of their lives (see Harvard Mental Health Letter, May 2009). In addition, advanced infertility treatments are expensive. The average cost of in vitro fertilization treatment in the U.S. is currently about $11,000 to $12,000 and even less aggressive treatments such as intrauterine insemination and ovarian stimulation can cost many hundreds to a few thousand dollars. There are no indications that rates of infertility are dropping or that this trend, increasing average age of first pregnancy, will reverse.

Reversing chronic conditions and enhancing desired physiological parameters remains an elusive goal of medicine. The modern medical paradigm based on blocking or promoting abnormal pathways offers symptomatic benefit, but tolerance to therapy can develop and treatment cessation can produce rebound symptoms and tachyphylaxis due to compensatory mechanisms.

SUMMARY

Methods of enhancing reproductive capacity in a female subject are provided. Aspects of the methods include inducing infertility in the subject in a manner effective to cause the subject to mount a compensatory response and thereby enhance reproductive capacity in the subject. Systems and kits useful in practicing the methods of the present disclosure are also provided.

Definitions

The term "fertility", as used herein, generally refers to the capacity to conceive or to induce conception of offspring. Accordingly, "infertility" generally refers to the inability to conceive or to induce conception of offspring. Infertility may be determined based on a duration of time, during which a mating couple or sexual partners having intercourse without contraception are unable to conceive offspring. In some instances, infertility may be indicated after a duration of about one year without conception. Female fertility may refer to the ability of a female to produce productive eggs or ova and/or the ability of a female to ovulate, i.e., discharge ova from the ovary. In some instances, infertility may be a result of menopause.

The term "menopause", as used herein, generally refers to the end of menstruation of a female subject. Menopause includes a decline in estrogen resulting in a wide range of changes in various tissues that respond to estrogen, such as e.g., vagina, vulva, uterus, bladder, urethra, breasts, bones, heart, blood vessels, brain, skin, hair, mucous membranes, and the like. The most common symptom of menopause is a change in the menstrual cycle, but other symptoms may occur, including but not limited to e.g., hot flashes, night sweats, insomnia, mood swings/irritability, memory or concentration problems, vaginal dryness, heavy bleeding, fatigue, depression, hair changes, headaches, heart palpitations, sexual disinterest, urinary changes and weight gain.

Menopause may be marked by the final period or ovulation cycle of the female subject, but is generally not an abrupt event, rather a gradual process. The clearest indication of menopause is the absence of an ovulation for one year, at which point a woman may be referred to as postmenopausal. It is also possible to diagnose menopause by testing hormone levels. One important test measures the levels of follicle-stimulating hormone (FSH), which steadily increases as a woman ages.

The age of menopause onset as well as the age of menopause completion may vary. Eight out of every 100 women will stop menstruating before age 40 and five out of every 100 women will continue to have periods until they are about 60 years of age. The average age of menopause is 51 and often occurs between the ages of 45 and 55. Menopause before the age of 40 may be referred to as premature menopause. Menopause before the age of 45 may be referred to as early menopause.

Some factors may be useful in predicting the onset and/or completion of menopause including but not limited to e.g., family history, body type, and lifestyle choices. The age at which menstruation began is not necessarily a predictor of when menopause will occur. For example, a woman beginning menstruation early or having entered puberty early will not necessarily experience early menopause.

The term "premenopause" generally refers to menstrual cycling that is relatively normal for a subject. A subject in premenopause may experience some gradual change in menstruation across a lifecycle, such as alteration in cycle length, changes in period pain or other premenstrual symptoms. However, during premenopause, on average, menstrual cycling will occur at regular intervals, including about monthly. The length of menstrual cycles may vary and may range from 21 to 45 days including 21 to 35 days in women of reproductive age, where the average cycle is 28 days.

The terms "perimenopause" or "menopausal transition" may be used interchangeably and generally refer to the interval in which many woman begin to experience one or more symptoms of menopause including e.g., irregular menstrual cycles. Perimenopause generally refers to the period just before menopause.

Further definitions and information related to menopause, including pre- and post-menopause may be found in Menopause: Full Guideline. NICE Guideline, No. 23. National Collaborating Centre for Women's and Children's Health (UK). London: National Institute for Health and Care Excellence (UK); 2015 Nov. 12; the disclosure of which is incorporated herein by reference in its entirety.

Whereas infertility and/or menopause, including premature menopause and early menopause, may not be classically considered diseases per se, for simplicity reference to diseases made herein will include fertility related conditions such as infertility, menopause, premature menopause, early menopause, and the like.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with infertility, e.g. those having infertility) as well as those in which prevention is desired (e.g., those with increased susceptibility to infertility; those subject to premature menopause; those suspected of having infertility; etc.).

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

A "therapeutically effective amount", a "therapeutically effective dose" or "therapeutic dose" is an amount sufficient to effect desired clinical results (i.e., achieve therapeutic efficacy, achieve a desired therapeutic response, etc.). A therapeutically effective dose can be administered in one or more administrations. For purposes of this disclosure, a therapeutically effective dose of an agent that enhances fertility and/or compositions is an amount that is sufficient, when administered to the individual, to palliate, ameliorate, stabilize, reverse, prevent, slow or delay the progression or onset of infertility by, for example, increasing the number of oogonia present in the ovary of the subject.

DETAILED DESCRIPTION

Methods of enhancing reproductive capacity in a female subject are provided. Aspects of the methods include inducing infertility in the subject in a manner effective to cause the subject to mount a compensatory response and thereby enhance reproductive capacity in the subject. Systems and kits useful in practicing the methods of the present disclosure are also provided.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

Methods

As summarized above, the instant disclosure provides methods of enhancing reproductive capacity in a female subject. The provided methods include inducing infertility in the subject in a manner effective to cause the subject to mount a compensatory response to enhance the reproductive capacity in the subject. Any convenient method of inducing infertility may find use in the subject methods, provided the induction allows for the subject to mount a compensatory response resulting in enhancement of the reproductive capacity of the subject. In some instances, reproductive capacity may also be referred to herein as fertility and the subject methods of enhancing reproductive capacity may thus include enhancing the fertility of a female subject through the herein described methods.

As the subject methods include inducing infertility of a subject as part of a method of enhancing reproductive capacity of the subject, the herein described methods may be considered to be paradoxical in approach. As such, the herein described methods include paradoxically enhancing fertility in a subject by inducing infertility of the subject may therefore also be referred to as methods of paradoxical reproductive enhancement.

In practicing the subject methods, the reproductive capacity of the subject is enhanced by inducing infertility in the subject, where the induction is of a nature and magnitude sufficient to achieve the desired enhancement. In certain embodiments, the induction is one of short duration, where by short duration is meant that the induction lasts for less than about 1 week, e.g., less than about 3 days, e.g., less than about 1 day, e.g., less than about 12 hours, where the duration of the induction may be even shorter. Where the induction includes administering a pharmacological agent, the duration refers to the period in which the pharmacological agent from an administered dosage is active. Where the stimulus is a physical regimen, the duration refers to the total of exercises performed by a subject over a given period, analogous to a dose of a pharmacological agent. Where the stimulus is a sleep regimen, the duration refers to the total of sleep modifications administered to a subject over a given period, analogous to a dose of a pharmacological agent. Where the induction includes administering an Eastern medicine, the duration refers to the period in which the administered Eastern medicine is active.

Following infertility induction, as described above, the fertility inducing stimulus is removed, e.g., by metabolization of the pharmacological agent or cessation of a physical, sleep-modification or Eastern medicine regimen, and the subject is permitted to mount a compensatory response. In this following period, no additional stimulus (e.g., fertility modulating pharmacological agent or an Eastern medicine) is administered to the subject or the subject's normal physical activity or sleep is not modulated. The duration of this period between stimulus application or physical or sleep modulation, which may be referred to as a "holiday" period, may vary, but in representative embodiments is at least about 1 day, such as at least about 2 days, including at least about 5 days, at least about 10 days, at least about 15 days, or longer. As such, embodiments of the methods include non-chronic (i.e., non-continuous) application of an infertility inducing stimulus, e.g., non-chronic administration of a pharmacologic agent, and/or non-chronic (i.e., non-continuous) modulation from the normal physical activity of a subject, non-chronic (i.e., non-continuous) modulation from the normal sleep regimen of a subject and/or non-chronic (i.e., non-continuous) administration of an Eastern medicine.

In certain embodiments, the methods include close monitoring or supervision of the subject during and/or after administration of a pharmacological agent, a physical regimen, a sleep regimen and/or an Eastern medicine. This monitoring may be completely automated, or at least in part performed manually, e.g., by a health care professional. For example, a health care professional can closely watch the subject following administration of a pharmacological agent, a physical regimen, a sleep regimen and/or an Eastern medicine as well as during the holiday period following. Based on this monitoring, such a health care professional may determine when a next administration should be performed. Monitoring also assures that the infertility inducement is not so severe as to be ultimately damaging to the subject at an unacceptable level.

Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In another example, following administration, a device that detects one or more aspects of a subject's physiology may input such data into an automated system, which uses the input parameters to automatically determine whether the subject is staying within a predetermined set of physiological parameters, or whether intervention is necessary. Accordingly, the methods may or may not require the subject to input monitored parameters, as such parameters may, in some instances, be automatically acquired.

In certain embodiments, the automated monitoring system may also be integrated with an administration device (e.g., a pharmacological delivery device, a sleep modulation device, etc.) or a device that directs the administration of a regimen (e.g., a physical regimen instructional device, a sleep regimen instructional device, etc.), such that the system, based on monitored parameters, determines when next to administer a infertility inducing agent or regimen, the duration of the next administration, etc. As such, the method may be characterized as inducing infertility for a first period in the subject and monitoring the subject for a response thereto. Following this first step, the method may further include at least a second period of induced infertility, wherein the second period is determined based on the monitored response to the first period.

In practicing the subject methods, the induction of infertility may vary, where in representative embodiments the induced infertility may be a pharmacological administration of an infertility inducing agent, administration of a physical regimen, administration of a sleep regimen or administration of an Eastern medicine. In the described methods, in some instances, such administrations may be solely pharmacologically based, solely physical regimen based, solely sleep regimen or solely Eastern medicine based. In the described methods, in some instances, such administrations may be some combination of pharmacological, physical and/or sleep regimen and/or Eastern medicine based. For example, in some instances, a subject method may include inducing infertility by administering a pharmacological agent to the subject and a physical regimen to the subject. In some instances, a subject method may include inducing infertility by administering a pharmacological agent to the subject and a sleep regimen to the subject. In some instances, a subject method may include inducing infertility by administering a physical regimen to the subject and a sleep regimen to the subject. In some instances, a subject method may include inducing infertility by administering a pharmacological agent to the subject, a physical regimen to the subject and a sleep regimen to the subject. In some instances, an Eastern medicine treatment may be included in any of the above combinations or a combination of Eastern medicine and one of pharmacological administration, physical regimen administration or sleep regimen administration may be employed.

The subject methods may include enhancing fertility in a variety of different subjects, including subjects having normal fertility (e.g., normal baseline fertility, normal average age-adjusted fertility, etc.) as well as subjects having some form of infertility. A variety of different infertility related conditions are treatable by the subject methods. Non-limiting examples of infertility related conditions include infertility that is a result of a disease, disorder or adverse health condition of the subject, including e.g., hormonal problems such as dysfunction of the hypothalamus or pituitary (e.g., resulting in a failure to produce mature eggs, a reduction in the production of mature eggs, or the like), ovarian cancer, ovarian cyst, polycystic ovary syndrome, premature ovarian failure, surface epithelial-stromal tumor, Brenner tumor, follicular cyst of ovary, ovarian torsion, ovarian disease, luteoma, hypogonadism, ovarian hyperthecosis, endometriosis of the ovary, ovarian hyperstimulation syndrome, Sertoli-Leydig cell tumor, etc., as well as those conditions not classically considered diseases such as e.g., menopause, premature menopause, early menopause, and the like.

Accordingly, in some instances, the subject methods include enhancing reproductive capacity in a healthy female subject by inducing infertility in the subject in a manner effective to cause the subject to mount a compensatory response. In some instances, the subject methods include enhancing reproductive capacity in an unhealthy female subject by inducing infertility in the subject in a manner effective to cause the subject to mount a compensatory response. In some instances, the subject may have some form or infertility, including infertility as a result of a disease or disorder as well as infertility as a result of the aging process, including e.g., menopause, or an abnormal menopause onset including e.g., early menopause or premature menopause. Induction of infertility in the subject methods may employ one or more of administering a pharmacological agent to the subject, administering a physical regimen to the subject, administering a sleep regimen to subject and/or administering Eastern medicine to the subject.

Increased fertility, as a result of the herein described methods, will generally include an increase in fertility relative to the subject's fertility prior to treatment, i.e., prior to any induction of infertility according to the methods described herein. As such, depending on the subject's baseline fertility (i.e., the unmodulated fertility of the subject prior to treatment according to the presently described methods) the enhanced fertility of the subject may be above, equal to, or below the average fertility of a normal healthy subject of comparable age and normal fertility.

As such the level of fertility enhancement will vary. For example, in some instances, a subject may have a baseline level of fertility that is below average and, as a result of the present methods, may have an enhanced level of fertility that remains below average but is higher than the subject's baseline level. In some instances, a subject may have a baseline level of fertility that is below average and, as a result of the present methods, may have an enhanced level of fertility that is equal to the average level of fertility for a comparable healthy, normal subject but is higher than the subject's baseline level. In some instances, a subject may have a baseline level of fertility that is below average and, as a result of the present methods, may have an enhanced level of fertility that is above average. In some instances, a subject may have a baseline level of fertility that is about equal to the average fertility of a normal, healthy individual and, as a result of the present methods, may have an enhanced level of fertility that is above average. In some instances, a subject may have a baseline level of fertility that is above that of a normal, healthy individual and, as a result of the present methods, may have an enhanced level of fertility that remains above average and is higher as compared to the subject's baseline level.

Administering a Pharmacological Agent

If a pharmacological approach is employed in inducing infertility, the specific nature and dosing schedule of the agent will vary depending on the particular nature of the infertility to be induced. Representative pharmacological agents that may find use in certain embodiments of the subject methods include but are not limited to contraceptives and other agents that prevent pregnancy or otherwise reduce fertility in a female subject.

In some embodiments, the subject invention includes administering an effective amount of a pharmacological agent to a subject. Any suitable pharmacological agents may be administered provided they induce infertility and allow the subject to mount a compensatory response. That is, embodiments of the subject methods include administering an effective amount, i.e., a therapeutically effective amount, of one or more pharmacological agents to a subject. By "effective amount" is meant a dosage sufficient to cause the subject to mount a compensatory response effective to enhance the fertility of the subject, as desired. The effective amount will vary with the age and physical condition of the subject, whether the subject has baseline normal fertility or infertility, the severity of infertility, if present, the duration of the treatment, the nature of any concurrent treatment, the pharmaceutically acceptable carrier used if any, and analogous factors within the knowledge and expertise of those skilled in the art.

In certain embodiments, more than one type of agent may be administered at the same or different times to treat the same or different condition. The effective amount of a given agent may vary somewhat from subject to subject, and may depend upon factors such as, but not limited to, the age and condition of the subject, the form of the agent, the route and method of delivery, etc., as noted above. Dosages may be determined in accordance with routine pharmacological procedures known to those skilled in the art.

Depending on the particular agent(s) administered to a subject, the agent(s) may be administered to a subject using any convenient means. Thus, a pharmacological agent may be incorporated into a variety of formulations for administration to a subject. A pharmacological agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the one or more pharmacological agents and other optional ingredients of the subject pharmacological agent compositions in that a pharmaceutically acceptable carrier may be combined with the pharmacological agent(s) without eliminating the biological or therapeutically effective activity of the one or more pharmacological agents, and is suitable for use in subjects as provided herein without undue adverse side effects (such as toxicity, irritation, allergic response, and death). Side effects are "undue" when their risk outweighs the benefit provided by the pharmaceutical agent.

Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the pharmacological agents employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperitoneal, transdermal, intracheal, intravaginal, endocervical, intrathecal, intranasal, intravesicular, in or on the eye, in the ear canal, etc., administration. In certain embodiments, one or more pharmacological agents may be administered via a transdermal patch or film system. In certain embodiments, one or more pharmacological agents may be administered via an intrauterine or intravaginal device such as or analogous to that described, e.g., in U.S. Pat. Nos. 9,427,351; 9,393,216; 9,370,574; 8,980,304; 6,159,491 and 6,416,778, the disclosures of which are herein incorporated by reference.

Embodiments may include pharmacological agent formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropyl-methyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological agent formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an aqueous or non-aqueous liquid; or as an oil-in-water or water-in-oil emulsion. Such pharmacological agent formulations may be prepared by any suitable method of pharmacy which includes, but is not limited to, bringing into association the active pharmacological agent and a suitable carrier (which may contain one or more optional ingredients as noted above). For example, pharmacological agent formulations for use with the subject invention may be prepared by uniformly and intimately admixing the active pharmacological agent(s) with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

Pharmacological agents may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include one or more pharmacological agent(s) made into suppositories by mixing with a variety of bases such as emulsifying bases or water—soluble bases.

Pharmacological agents may also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include at least one pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, the one or more pharmacological agent agents may be utilized in aerosol formulation or an analogous formulation to be administered via inhalation or analogous means. The one or more pharmacological agents employed in the practice of the present invention may be formulated into pressurized acceptable propellants such as dichlorodifluoromethane, propane, nitrogen and the like.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. Pharmacological agent formulations suitable for transdermal administration may also be delivered by iontophoresis and may take the form of an optionally buffered aqueous solution of the pharmacological agent compound. Suitable formulations may include citrate or bis/tris buffer (pH 6) or ethanol/water and contain a suitable amount of active ingredient.

Pharmacological agents may be provided as a salt and may be formed with one or more acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Pharmacological agents may be administered parenterally, such as intravenous (IV) administration, and may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological agent formulations suitable for parenteral administration may include sterile aqueous and non-aqueous injection solutions of one or more active pharmacological agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

Pharmacological agents may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). Accordingly, embodiments may include one or more pharmacological agents administered as liposomal formulations of the pharmacological agents. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

A pharmaceutical composition of the subject invention may optionally contain, in addition to a pharmacological agent, at least one other therapeutic agent useful in the treatment of a condition. Such other compounds may be of any class of drug or pharmaceutical agent, including but not limited to antibiotics, anti-parasitic agents, antifungal agents, anti-viral agents, anti-tumor agents, anti-neurodegenerative agents and anti-psychotic agents. When administered with anti-parasitic, anti-bacterial, anti-fungal, anti-tumor, anti-viral agents, anti-neurodegenerative, and anti-psychotic agents and the like, pharmacological agents may be administered by any method and route of administration suitable to the treatment of the condition, typically as pharmaceutical compositions.

Pharmacological agents may include compositions that may be prepared from water-insoluble compounds, or salts thereof, such as aqueous base emulsions. In such embodiments, the pharmacological agent composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological agents, the compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multi-dose use. Pharmacological agent compositions for use in practicing the subject methods may be lyophilized using techniques well known in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmaceutical agent administration device include instruments of containment that may be used to deliver, place, attach, and/or insert at least one pharmacological agent into the delivery device for administration of the pharmacological agent to a subject and include, but are not limited to, vials, ampules, tubes, capsules, bottles, syringes and bags.

In certain embodiments, a pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological agent formulations include, but are not limited to, formulations that include one or more active pharmacological agents and physiological saline solution (optionally including other typical ingredients such as other active agents and buffers).

As noted above, in pharmaceutical dosage forms, agents may be administered alone or with an appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time. The pharmacological agent and at least one other adjuvant may be administered simultaneously (i.e., concurrently) or sequentially. Simultaneous administration may be carried out by mixing at least one pharmacological agent and at least one other adjuvant prior to administration, or by administering the pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent calculated in an amount sufficient to produce the desired effect in association with a pharmaceutically acceptable diluent, carrier or vehicle. The specifications for the unit dosage forms of pharmacological agents of the present invention depend on, for example, the particular pharmacological agent(s) employed and the effect to be achieved, the pharmacodynamics associated with the particular pharmacological agent(s) in the subject, etc.

Embodiments include administering an effective amount of a first agent and an effective amount of a second agent. For example, embodiments may include administering a first agent and a second agent to provide an enhanced therapeutic effect. By "enhanced therapeutic effect" is meant that at least the desired outcome occurs more quickly and/or is of greater magnitude with a combination of the pharmacological agents, as compared to the same doses of each component given alone; or that doses of one or all component(s) are below what would otherwise be a minimum effective dose (a "sub-MED").

Any two pharmacological agents may be given in close enough temporal proximity to allow their individual therapeutic effects to overlap. For example, embodiments of the subject invention include the co-timely administration of a first and second agent, where "co-timely" is meant administration of a second pharmacological agent while a first pharmacological agent is still present in a subject in a therapeutically effective amount. It is to be understood that in some instances this will require sequential administration. Alternatively, multiple routes of administration may be employed, e.g., intravenous or subcutaneous injection combined with oral administration, and the like.

Embodiments also include pharmaceutical compositions in unit dosage forms that are useful which contain more than one type of pharmacological agent. In other words, a single agent administration entity may include two or more pharmacological agents. For example, a single tablet, capsule, dragee, trocheem suppository, syringe, and the like, combining two or more pharmacological agents would be a unit dosage form. The therapeutic agents present in a unit dosage form may be present in amounts such that, upon administration of one or more unit doses of the composition, a subject experiences, e.g., a longer lasting efficacy than with the administration of either agent alone and/or greater magnitude and/or quicker lowering of action. Such compositions may be included as part of a therapeutic package in which one or more unit doses are placed in a finished pharmaceutical container. Labeling may be included to provide directions for using the composition according to the invention. The actual amounts of each agent in such single unit dosage forms may vary according to the specific compositions being utilized, the particular compositions formulated, the mode of application, the particular route of administration, and the like, where dosages for a given subject may be determined using conventional considerations, e.g., by customary comparison of the differential activities of the subject compositions and of a known agent, or by means of an appropriate, conventional pharmacological protocol.

Any convenient pharmacological agent that induces infertility in a female subject in a manner effective to cause the subject to mount a compensatory response may be employed in pharmacological modulation according to the methods of the present disclosure. Useful pharmacological agents include e.g., contraceptives, including but not limited to e.g., oral contraceptives, transdermal contraceptives, intradermal contraceptives, intrauterine contraceptives, intravaginal contraceptives, injected contraceptives (e.g., intramuscular injected contraceptives), and the like. Non-limiting examples of useful contraceptives include desogestrel/ethinyl estradiol systemic, dienogest/estradiol systemic, drospirenone/ethinyl estradiol systemic, drospirenone/ethinyl estradiol/levomefolate calcium systemic, estradiol/medroxyprogesterone systemic, ethinyl estradiol/ethynodiol systemic, ethinyl estradiol/etonogestrel systemic, ethinyl estradiol/folic acid/levonorgestrel systemic, ethinyl estradiol/levonorgestrel systemic, ethinyl estradiol/norelgestromin systemic, ethinyl estradiol/norethindrone systemic, ethinyl estradiol/norgestimate systemic, ethinyl estradiol/norgestrel systemic, etonogestrel systemic, levonorgestrel systemic, medroxyprogesterone systemic, mestranol/norethindrone systemic, norethindrone systemic, including brand name versions such as e.g., Afirmelle, Alesse, Altavera, Alyacen 1/35, Alyacen 7/7/7, Amethia, Amethia Lo, Amethyst, Apri, Aranelle, Ashlyna, Aubra, Aviane, Aygestin, Ayuna, Azurette, Balziva, Bekyree, Beyaz, Blisovi 24 Fe, Blisovi Fe 1.5/30, Blisovi Fe 1/20, Brevicon, Briellyn, Camila, Camrese, CamreseLo, Caziant, Cesia, Chateal, Cryselle, Cyclafem 1/35, Cyclafem 7/7/7, Cyclessa, Cyonanz, Cyred, Dasetta 1/35, Dasetta 7/7/7, Daysee, Delyla, Demulen, Depo-Provera, Depo-Provera Contraceptive, depo-subQ provera 104, Desogen, Elinest, Emoquette, Enpresse, Enskyce, Errin, Estarylla, Estrostep Fe, Falmina, Fayosim, Femcon Fe, femhrt, Femynor, Fyavolv, Generess Fe, Gianvi, Gildagia, Gildess 1.5/30, Gildess 1/20, Gildess 24 Fe, Gildess Fe 1.5/30, Gildess Fe 1/20, Implanon, Introvale, Isibloom, Jencycla, Jevantique, Jevantique Lo, Jinteli, Jolessa, Jolivette, Juleber, Junel 1.5/30, Junel 1/20, Junel Fe 24, Kaitlib Fe, Kariva, Kelnor 1/35, Kimidess, Kurvelo, Larin 1.5/30, Larin 1/20, Larin 24 Fe, Larin Fe 1.5/30, Larin Fe 1/20, Larissia, Layolis Fe, Leena, Lessina, Levlen, Levlite, Levonest, Levonest-28, Levora, Liletta, Lillow, Lo Loestrin Fe, Lo Minastrin Fe, Lo Simpesse, Lo/Ovral, Lo/Ovral-28, Loestrin 1/20, Loestrin 21 1.5/30, Loestrin 24 Fe, Loestrin Fe 1/20, Lomedia 24 Fe, Loryna, LoSeasonique, Low-Ogestrel-21, Lunelle, Lutera, Lybrel, Lyza, Marlissa, Mibelas 24 Fe, Microgestin 1.5/30, Microgestin 1/20, Microgestin 24 Fe, Microgestin Fe 1/20, Mili, Minastrin 24 Fe, Mircette, Mirena, Modicon, Mono-Linyah, Mononessa, My Way, Myzilra, Natazia, Necon 0.5/35, Necon 1/35, Necon 1/50, Necon 7/7/7, Nexesta Fe, Nexplanon, Next Choice, Nor-QD, Nora-Be, Nordette, Norinyl 1+50, Nortrel 1/35, Nortrel 7/7/7, NuvaRing, Nylia 1/35, Nylia 7/7/7, Ocella, Ogestrel, Ogestrel-28, Orsythia, Ortho Cyclen, Ortho Evra, Ortho Micronor, Ortho Tri-Cyclen, Ortho Tri-Cyclen Lo, Ortho-Cept, Ortho-Novum 1/35, Ortho-Novum 1/50, Ortho-Novum 7/7/7, Ovcon 35, Philith, Pimtrea, Pirmella 1/35, Pirmella 7/7/7, Plan B, Plan B One-Step, Portia, Preven EC, Previfem, Provera, Quartette, Quasense, Reclipsen, Rivelsa, Safyral, Seasonale, Seasonique, Setlakin, Simliya, Simpesse, Skyla, Solia, Sprintec, Sronyx, Syeda, Tarina Fe 1/20, Taytulla, Tilia Fe, Tri Femynor, Tri-Estarylla, Tri-Legest, Tri-Legest Fe, Tri-Linyah, Tri-Lo-Estarylla, Tri-Lo-Marzia, Tri-Lo-hili, Tri-Lo-Sprintec, Tri-Mili, Tri-Norinyl, Tri-Previfem, Tri-Sprintec, TriNessa, Tri-Nessa Lo, Triphasil, Triphasil-21, Triphasil-28, Trivora, Trivora-28, Velivet, Vestura, Vienva, Viorele, Vyfemla, Wera, Wymzya Fe, Yasmin, Yaz, Zarah, Zenchent, Zenchent Fe, Zeosa, Zovia, Zovia 1/35, Zovia 1/50, and the like.

Useful dosages of pharmacological agents in the subject methods will vary depending on the agent employed, the state of the subject (e.g., whether the subject is baseline fertile or baseline infertile), etc. In some instances, where a contraceptive agent is employed, a useful dosage may include the dosage commonly employed for contraception. In some instances, a useful dosage may be higher or lower than the dosage commonly employed for contraception, including but not limited to less than 10% of the dosage employed for contraception or more than 200% of the dosage employed for contraception. Useful dosages of contraceptives may, in some instances, range from 10% to 200% of the dosage employed for contraception, including but not limited to e.g., from 10% to 200%, from 20% to 200%, from 30% to 200%, from 40% to 200%, from 50% to 200%, from 60% to 200%, from 70% to 200%, from 80% to 200%, from 90% to 200%, from 100% to 200%, from 110% to 200%, from 120% to 200%, from 130% to 200%, from 140% to 200%, from 150% to 200%, from 160% to 200%, from 170% to 200%, from 180% to 200%, from 190% to 200%, from 10% to 190%, from 10% to 180%, from 10% to 170%, from 10% to 160%, from 10% to 150%, from 10% to 140%, from 10% to 130%, from 10% to 120%, from 10% to 110%, from 10% to 100%, from 10% to 90%, from 10% to 80%, from 10% to 70%, from 10% to 60%, from 10% to 50%, from 10% to 40%, from 10% to 30%, from 10% to 20%, from 20% to 180%, from 30% to 170%, from 40% to 160%, from 50% to 150%, from 60% to 140%, from 70% to 130%, from 80% to 120%, from 90% to 110%, etc., of the dosage employed for contraception.

Administering a Physical Regimen

As summarized above, some embodiments may include employing a physical regimen, in a manner effective to cause the desired enhancement according to the subject methods. Useful physical regimens include those that, when administered to a subject, induce infertility in the subject.

If a physical regimen modulating approach is employed in inducing infertility, the specific nature of the physical regimen will vary depending on the particular nature of the infertility to be induced. Representative physical regimens that may find use in certain embodiments of the subject methods include but are not limited to daily, weekly, monthly, etc., physical activity regimens that prevent or otherwise inhibit pregnancy or otherwise reduce fertility in a female subject.

Non-limiting examples of physical activity that may be employed in a physical regimen to induce infertility include e.g., high levels of vigorous exercise, including e.g., running, swimming, cycling, weight lifting, gymnastics, and the like. Physical regimens may employ one or more of the subject activities at a sufficient frequency to induce infertility in a subject. The amount of physical activity sufficient to induce infertility will vary depending on various factors, including e.g., the health status of the subject at the time the physical regimen is employed, where e.g., healthy individuals with exceptional cardiovascular fitness may require a higher level of activity and/or more frequent activity as compared to subjects with normal or average cardiovascular fitness.

In some instances, a subject physical regimen may include five hours or more hours of rigorous physical activity per week, including but not limited to e.g., 6 or more hours per week, 6 or more hours per week, 7 or more hours per week, 8 or more hours per week, 9 or more hours per week, 10 or more hours per week, 11 or more hours per week, 12 or more hours per week, 13 or more hours per week, 14 or more hours per week, 15 or more hours per week, 16 or more hours per week, 17 or more hours per week, 18 or more hours per week, 19 or more hours per week, 20 or more hours per week, 21 or more hours per week, 22 or more hours per week, 23 or more hours per week, 24 or more hours per week, 25 or more hours per week, 26 or more hours per week, 27 or more hours per week, 28 or more hours per week, 29 or more hours per week, 30 or more hours per week, 31 or more hours per week, 32 or more hours per week, 33 or more hours per week, 34 or more hours per week, 35 or more hours per week, 36 or more hours per week, 37 or more hours per week, 38 or more hours per week, 39 or more hours per week, 40 or more hours per week, 41 or more hours per week, 42 or more hours per week, etc.

In some instances, a subject physical regimen may include rigorous physical activity of three or more times per week, including but not limited to 4 or more times per week, 5 or more times per week, 6 or more times per week, 7 or more times per week, 8 or more times per week, 9 or more times per week, 10 or more times per week, 11 or more times per week, 12 or more times per week, 13 or more times per week, 14 or more times per week, 15 or more times per week, 16 or more times per week, 17 or more times per week, 18 or more times per week, 19 or more times per week, 20 or more times per week, 21 or more times per week, etc.

The level of physical exertion of an activity required to reach the level of rigorous physical activity will depend on a number of factors depending on the individual and the activity including e.g., the subject's general state of health, the altitude at which the activity is performed, the type of activity chosen, and the like. In some instances, a subject physical regimen will include activity at greater than 69% of a subject's maximum average heart rate, including but not limited to e.g., activity at 70% or greater than the subject's maximum heart rate, activity at 75% or greater than the subject's maximum heart rate, activity at 80% or greater than the subject's maximum heart rate, activity at 85% or greater than the subject's maximum heart rate, activity at 90% or greater than the subject's maximum heart rate, etc., In some instances, depending on the length of time the activity is performed and/or the frequency at which the activity is performed, the activity may generally be performed at less than 95% of the subject's maximum heart rate.

As subject's maximum heart rate may be determined empirically, e.g., through a laboratory test such as e.g., maximal treadmill and bicycle stress tests, or a field test. In some instances, a subject's maximum heart rate may be estimated, e.g., based on the average maximum heart rate for subject of a particular age. Non-limiting examples of maximum heart rates for health individuals of various ages include: 200 beats per minute for subjects of 20 years of age, 190 beats per minute for subjects of 30 years of age, 185 beats per minute for subjects of 35 years of age, 180 beats per minute for subjects of 40 years of age, 175 beats per minute for subjects of 45 years of age, 170 beats per minute for subjects of 50 years of age, 165 beats per minute for subjects of 55 years of age, 160 beats per minute for subjects of 60 years of age, 155 beats per minute for subjects of 65 years of age, 150 beats per minute for subjects of 70 years of age, etc. In some instances, the maximum heart rate of an individual may be estimated as about 220 beats per minute minus the subject's age.

A physical regimen sufficient to induce infertility in a subject may be devised generally for individuals of particular common characteristics, e.g., height, weight, percent body fat, body mass index (BMI), age, etc. In some instances, a medical provider may provide a physical regimen sufficient to induce infertility in a subject according to the subject's particular characteristics, including e.g., a medical history, current state of physical fitness, etc.

Administration of a physical regimen to a subject may include a medical provider, or other health consultant, prescribing a particular physical activity schedule to a subject containing a sufficient rigorous physical activity to induce infertility in the subject. In some instances, physical activity modulating device may be used or provided to the subject. As used herein a "physical activity modulating device" generally describes any device that instructs or otherwise prompts an individual to perform activities of a physical regimen. Accordingly, a physical activity modulating device may include a physical regimen stored thereon such that the device may instruct a user to perform the physical activities of the regimen. In some instances, such a device may be an electronic device such as a computer that includes one or more sensors (e.g., motion sensors, heat rate sensors, etc.) for monitoring the activity of a subject. Physical activity modulating devices may include one or more physical regimens stored thereon, e.g., in software or other computer readable format (including non-transitory formats), to which monitored physical activity is compared. In some instances, a physical activity modulating device may prompt or prod a user to perform one or more activities, according to a physical regimen, to induce infertility in the subject. As such, physical activity modulating devices may include one or more user interfaces, including e.g., a screen, a touch screen, a speaker, a buzzer or alarm, a button, a dial, a keyboard, a track-ball, an electrode, and the like. In some instances, a physical activity modulating device may be wearable (e.g., a watch, a necklace, an ankle band, a wrist band, etc.). In some instances, a physical activity modulating device may interface with a computing device such as a computer.

Physical regimens may further include a holiday period. Such a holiday period in a physical regimen will generally an "off" period where rigorous physical activity is not performed. A "holiday period", may vary, but in representative embodiments is at least about 1 day, such as at least about 2 days, including at least about 5 days, at least about 10 days, at least about 15 days, or longer. In some instances, a holiday period may be 1 week or more, including but not limited to e.g., 2 weeks or more, 3 weeks or more, a month or more, 2 months or more, 3 months or more, 4 months or more, 5 months or more, 6 months or more, 7 months or more, 8 months or more, 9 months or more, 10 months or more, 11 months or more, a year or more, 2 years or more, 3 years or more, 4 years or more, etc. As such, embodiments of the methods include non-chronic (i.e., non-continuous) administration of the physical regimen, e.g., non-chronic administration of the physical regimen for enhancing fertility.

During the holiday period a subject may be permitted to mount a compensatory response to the infertility induced by the physical regimen. In some instances, a physical activity modulating device may be programmed to include one or more holiday periods as part of the overall physical regimen programmed into the device.

Administering a Sleep Regimen

As summarized above, some embodiments may include employing a sleep regimen, in a manner effective to cause the desired enhancement according to the subject methods. Useful sleep regimens include those that, when administered to a subject, induce infertility in the subject.

If a sleep regimen modulating approach is employed in inducing infertility, the specific nature of the sleep regimen will vary depending on the particular nature of the infertility to be induced. Representative sleep regimens that may find use in certain embodiments of the subject methods include but are not limited to daily, weekly, monthly, etc., sleep activity regimens that prevent or otherwise inhibit pregnancy or otherwise reduce fertility in a female subject.

Non-limiting examples of sleep modulation that may be employed in a sleep regimen to induce infertility include e.g., sleep deprivation, sleep inversion or sleep-wake inversion and the like. Sleep regimens may employ one or more of the subject modulations at a sufficient frequency to induce infertility in a subject. The amount of sleep modulation sufficient to induce infertility will vary depending on various factors, including e.g., the health status of the subject at the time the sleep regimen is employed, the normal sleep patterns of the subject, etc., where e.g., subject with normally longer (e.g., 8 plus hours per night) sleep patterns may require less sleep pattern modulation than subjects having normally shorter (e.g., less than 8 hours per night) sleep patterns.

In some instances, a subject sleep regimen may include preventing and/or instructing the subject to sleep less than eight hours of sleep a night, including but not limited to e.g., less than 7 hours per night, less than 6 hours per night, less than 5 hours per night, less than 4 hours per night, etc. In some instances, a subject sleep regimen may include preventing and/or instructing the subject to sleep less than 50 hours of sleep a week, including but not limited to e.g., less than 49 hours per week, less than 48 hours per week, less than 47 hours per week, less than 46 hours per week, less than 45 hours per week, less than 44 hours per week, less than 43 hours per week, less than 42 hours per week, less than 41 hours per week, less than 40 hours per week, less than 39 hours per week, less than 38 hours per week, less than 37 hours per week, less than 36 hours per week, less than 35 hours per week, etc. In some instances, a subject sleep regimen may include subjecting the subject to one or more periods of wakefulness during nighttime hours, including 2 or more periods per night, 3 or more periods per night, 4 or more periods per night, etc. Where employed, the length of periods of wakefulness will vary and may range from less than 30 min. to 2 hours or more, including but not limited to e.g., 30 min. to 2 hours, 30 min. to 1.5 hours, 30 min. to 1 hour, 30 min. to 45 min., 45 min. to 2 hours, 45 min. to 1.5 hours, 45 min. to 1 hour, 1 hour to 2 hours, 1 hour to 1.5 hours, 1.5 hours to 2 hours, and the like.

In some instances, e.g., where a sleep regimen is structured on a weekly basis, such a regimen may include a certain number of sleep modulations per week including but not limited to e.g., 4 or more times per week, 5 or more times per week, 6 or more times per week, 7 or more times per week, 8 or more times per week, 9 or more times per week, 10 or more times per week, 11 or more times per week, 12 or more times per week, 13 or more times per week, 14 or more times per week, 15 or more times per week, 16 or more times per week, 17 or more times per week, 18 or more times per week, 19 or more times per week, 20 or more times per week, 21 or more times per week, etc.

As summarized above, in some instances, a sleep regimen to induce infertility may include periods of sleep inversion or sleep-wake inversion. As used herein "sleep inversion" and "sleep-wake inversion" will generally refer to periods of time where a subject is permitted to or instructed to sleep during daytime hours and remain wakeful during nighttime hours. Sleep-wake inversion may be administered independently or in combination with sleep deprivation. In some instances, a sleep regimen may include a period of sleep-wake inversion of one week or more, including but not limited to e.g., at least about 10 days, at least about 15 days, or longer. In some instances, a period of sleep-wake inversion may be 2 weeks or more, including but not limited to e.g., 3 weeks or more, a month or more, 2 months or more, 3 months or more, 4 months or more, 5 months or more, 6 months or more, 7 months or more, 8 months or more, 9 months or more, 10 months or more, 11 months or more, a year or more, etc.

A sleep regimen sufficient to induce infertility in a subject may be devised generally for individuals of particular common characteristics, e.g., height, weight, percent body fat, body mass index (BMI), age, average nightly sleep, etc. In some instances, a medical provider may provide a sleep regimen sufficient to induce infertility in a subject according to the subject's particular characteristics, including e.g., a medical history, current state of fitness, current nightly sleep, etc.

Administration of a sleep regimen to a subject may include a medical provider, or other health consultant, prescribing a particular sleep modulation schedule to a subject containing a sufficiently disruptive sleep modulation(s) to induce infertility in the subject. In some instances, a sleep modulating device may be used or provided to the subject.

As used herein a "sleep modulating device" generally describes any device that instructs or otherwise prompts or stimulates an individual to modulate the subject's sleep consistent with a sleep regimen described herein. Accordingly, a sleep modulating device may include a sleep regimen stored thereon such that the device may instruct, prompt or stimulate a user to perform the sleep modulation of the regimen. Sleep modulations of such a device may include an alarm configured to wake the user and/or indicate to a user when to reinitiate sleep, instructions as to when a user should initiate sleep and/or terminate sleep, a stimulatory device (e.g., an electrical stimulator) of sufficient strength to wake the user according to the programed sleep modulation, and the like.

In some instances, a sleep modulating device may be an electronic device such as a computer that includes one or more sensors (e.g., motion sensors, heat rate sensors, brain wave sensors, respiratory sensors, etc.) for monitoring the sleep of a subject. Sleep modulating devices may include one or more sleep regimens stored thereon, e.g., in software or other computer readable format (including non-transitory formats), to which monitored sleep is compared. In some instances, a sleep modulating device may prompt or prod a user to perform one or more activities (e.g., awake, attempt sleep, etc.), according to a sleep regimen, to induce infertility in the subject. As such, sleep modulating devices may include one or more user interfaces, including e.g., a screen, a touch screen, a speaker, a buzzer or alarm, a button, a dial, a keyboard, a track-ball, an electrode, and the like. In some instances, a sleep modulating device may be wearable (e.g., a watch, a necklace, an ankle band, a wrist band, a headband, a hat, etc.). In some instances, a sleep modulating device may interface with a computing device such as a computer.

Sleep regimens may further include a holiday period. Such a holiday period in a sleep regimen will generally an "off" period where sleep modulation is not performed (i.e., a subject may be permitted to sleep ad libitum or may be instructed to sleep at least 7 hours or more per night, including e.g., 8 hours or more). A "holiday period", may vary, but in representative embodiments is at least about 1 day, such as at least about 2 days, including at least about 5 days, at least about 10 days, at least about 15 days, or longer. In some instances, a holiday period may be 1 week or more, including but not limited to e.g., 2 weeks or more, 3 weeks or more, a month or more, 2 months or more, 3 months or more, 4 months or more, 5 months or more, 6 months or more, 7 months or more, 8 months or more, 9 months or more, 10 months or more, 11 months or more, a year or more, 2 years or more, 3 years or more, 4 years or more, etc. As such, embodiments of the methods include non-chronic (i.e., non-continuous) administration of the sleep regimen, e.g., non-chronic administration of the sleep regimen for enhancing fertility.

During the holiday period a subject may be permitted to mount a compensatory response to the infertility induced by the sleep regimen. In some instances, a sleep modulating device may be programmed to include one or more holiday periods as part of the overall sleep regimen programmed into the device.

Eastern Medicine

As summarized above, some embodiments may include administering Eastern medicine, in a manner effective to cause the desired enhancement according to the subject methods. Useful Eastern medicines include those that, when administered to a subject, induce infertility in the subject. As used herein the term "Eastern medicine" generally includes medical treatments originating on the Asian continent involving the use herbal medicines and various mind and body practices, such as acupuncture and tai chi, to treat or prevent health problems. Useful Eastern medicines may include e.g., Traditional Chinese medicine. Useful Eastern medicines will vary and, in some instances, methods of the present disclosure may involve acupuncture, acupressure, moxibustion, cupping therapy, and the like, which may be performed independently or in combination. Techniques for the application of acupuncture and acupressure will vary and may include e.g., traditional needling (e.g., insertion with or without needle manipulation, e.g., plucking, shaking or trembling), electroacupuncture, fire needle acupuncture, sonopuncture, acupuncture point injection, auriculotherapy, scalp acupuncture, hand acupuncture, and the like. In some instances, useful Eastern medicine approaches may include stimulation (e.g., by acupuncture, acupressure, or the like) of one or more forbidden acupuncture points in pregnancy or other acupressure or acupuncture points that are contraindicated for fertility. For forbidden points for stimulation (e.g., using acupressure and/or acupuncture and/or other methods such as moxibustion, alone or in combination) that are contraindicated in certain instances include but are not limited to e.g., LU 11, LU 10, LI 4, LI 15, LI 19, LI 20, ST1, ST 2, ST 7, ST 8, ST 9, ST 17, ST 25, ST 32, SP 2, SP 6, SP 7, HT 1, HT 2, SI 10, SI 11, SI 18, BL 1, BL 2, BL 6, BL 49, BL 51, BL 54, BL 56, BL 60, BL 62, BL 67, KI 11, P(CX)8, TH 7, TH 8, TH 16, TH 19, TH 23, GB 1, GB 3, GB 4, GB 5, GB 15, GB 18, GB 21, GB 22, GB 33, GB 42, LIV 12, CV 4, CV 5, CV 8, CV 11, CV 14, CV 15, CV 17, GV 4, GV 6, GV 11, GV 15, GV 16, GV 17, GV 23, GV 24, GV 26, GV 28, and the like. In some instances, contraindicated points (e.g., as contraindicated in pregnancy and/or fertility) may include those described in e.g., Betts & Budd, Acupuncture in Medicine Published Online First: 27 Mar. 2011. doi: 10.1136/aim.2010.003814 and Blum J E, *Woman heal thyself: an ancient healing system for contemporary women*. Boston: Charles E. Tuttle, 1996; the disclosures of which are incorporated herein by reference in their entirety.

If an Eastern medicine approach is employed in inducing infertility, the specific nature of the Eastern medicine will vary depending on the particular nature of the infertility to be induced. Representative Eastern medicine approaches that may find use in certain embodiments of the subject methods include but are not limited to daily, weekly, monthly, etc., application of Eastern medicine techniques, such as acupuncture and acupressure, that prevent or otherwise inhibit pregnancy or otherwise reduce fertility in a female subject.

Non-limiting examples of Eastern medicine administrations that may be employed to induce infertility include e.g., acupuncture and/or acupressure of points contraindicated for fertility and/or promotion of pregnancy.

Acupuncture and/or acupressure may employ one or more of the subject modulations at a sufficient frequency to induce infertility in a subject. The amount of acupuncture and/or acupressure sufficient to induce infertility will vary depending on various factors, including e.g., the health status of the subject at the time the acupuncture and/or acupressure is employed, the position in the menstrual cycle of the subject, etc., where e.g., subject at one position in the menstrual cycle may require stimulation of one or more points contraindicated for fertility and/or pregnancy and a subject at a different position in the menstrual cycle may require stimulation of one or more different points contraindicated for fertility and/or pregnancy. In some instances, the points contraindicated for fertility and/or pregnancy may be independent of a subject's position in the menstrual cycle.

In some instances, e.g., where a Eastern medicine regimen is structured on a weekly basis, such a regimen may include a certain number of treatments per week including but not limited to e.g., 1 or more times per week, 2 or more times per week, 3 or more times per week, 4 or more times per week, 5 or more times per week, 6 or more times per week, 7 or more times per week, 8 or more times per week, 9 or more times per week, 10 or more times per week, 11 or more times per week, 12 or more times per week, 13 or more times per week, 14 or more times per week, 15 or more times per week, 16 or more times per week, 17 or more times per week, 18 or more times per week, 19 or more times per week, 20 or more times per week, 21 or more times per week, etc.

Eastern medicine treatments may be administered independently or in combination with various different types of Eastern medicine treatments. For example, acupuncture may be administered alone or in combination with acupressure. In some instances, an Eastern medicine treatment may include a treatment schedule lasting one week or more, including but not limited to e.g., at least about 10 days, at least about 15 days, or longer. In some instances, an Eastern medicine treatment schedule may span 2 weeks or more, including but not limited to e.g., 3 weeks or more, a month or more, 2 months or more, 3 months or more, 4 months or more, 5 months or more, 6 months or more, 7 months or more, 8 months or more, 9 months or more, 10 months or more, 11 months or more, a year or more, etc.

An Eastern medicine treatment schedule sufficient to induce infertility in a subject may be devised generally for individuals of particular common characteristics, e.g., height, weight, percent body fat, body mass index (BMI), age, etc. In some instances, a medical provider may provide an Eastern medicine treatment schedule sufficient to induce infertility in a subject according to the subject's particular characteristics, including e.g., a medical history, current state of fitness, prior Eastern medicine treatments, etc.

Administration of an Eastern medicine treatment schedule to a subject may include a medical provider, or other health consultant, prescribing and or administering a particular Eastern medicine treatment or treatments to a subject to induce infertility in the subject. In some instances, an administration of an Eastern medicine treatment may involve the use of an Eastern medicine delivery device, which may be used by or provided to the subject.

As used herein a "an Eastern medicine delivery device" generally describes any device that delivers and application of Eastern medicine to an individual to stimulate the subject consistent with an Eastern medicine treatment schedule described herein. Accordingly, an Eastern medicine delivery device may include an Eastern medicine treatment schedule stored thereon such that the device may instruct, prompt, administer and/or stimulate a user as required by the treatment schedule. Such a device may include one or more acupressure inducing components that provides acupressure to a specific acupressure point according to the treatment schedule. In some instances, a subject device may include one or more needles and/or needle-connected electrodes for stimulating one or more specific acupuncture points according to the treatment schedule.

In some instances, an Eastern medicine delivery device may be an electronic device such as a computer that includes one or more sensors for monitoring a subject. Eastern medicine delivery devices may include one or more treatment schedules stored thereon, e.g., in software or other computer readable format (including non-transitory formats), with which physiological information pertaining to the subject obtained from a sensor of the device may be integrated. As such, subject Eastern medicine delivery devices may or may not integrate a subject's physiological parameters into the subject treatment that is applied. In some instances, an Eastern medicine delivery device may be wearable and in other instances such device may be a table-top or free standing device. In some instances, an Eastern medicine delivery device may interface with a computing device.

Eastern medicine treatment schedules may further include a holiday period. Such a holiday period in a treatment schedule will generally be an "off" period where the Eastern medicine is not administered. A "holiday period", may vary, but in representative embodiments is at least about 1 day, such as at least about 2 days, including at least about 5 days, at least about 10 days, at least about 15 days, or longer. In some instances, a holiday period may be 1 week or more, including but not limited to e.g., 2 weeks or more, 3 weeks or more, a month or more, 2 months or more, 3 months or more, 4 months or more, 5 months or more, 6 months or more, 7 months or more, 8 months or more, 9 months or more, 10 months or more, 11 months or more, a year or more, 2 years or more, 3 years or more, 4 years or more, etc. As such, embodiments of the methods include non-chronic (i.e., non-continuous) administration of the Eastern medicine, e.g., non-chronic administration of the Eastern medicine for enhancing fertility.

During the holiday period a subject may be permitted to mount a compensatory response to the infertility induced by the Eastern medicine. In some instances, an Eastern medicine delivery device may be programmed to include one or more holiday periods as part of the overall treatment schedule programmed into the device.

Combination Methods

As summarized above, in some instances, combined methods may be employed, including e.g., where a subject is administered some combination of a pharmacological agent, a physical regimen, a sleep regimen and/or Eastern medicine. According, the individual techniques of the methods described herein may be co-administered and/or administered in combination with one or more conventional methods of modulating fertility, including e.g., conventional agents for treating infertility or diseases associated with infertility. By conventional agents for treating infertility is meant agents known in the art that prevent or inhibit infertility or dysfunction of the reproductive organs including but not limited to, e.g., gonadotropin-releasing hormone, oestrogen antagonists, gonadotropins and the like.

The terms "co-administration" and "in combination with" include the administration of two or more therapeutic agents and/or regimens either simultaneously, concurrently or sequentially within no specific time limits. In one embodiment, the agents and or regiments are present in the cell or in the subject's body or applied to the subject at the same time or exert their biological or therapeutic effect at the same time. In one embodiment, multiple therapeutic agents are in the same composition or unit dosage form. In other embodiments, multiple therapeutic agents are in separate compositions or unit dosage forms. In certain embodiments, a first agent or regimen can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent or regimen.

In some instances, administration of an amount of an agent or administration of a regiment may be combined with one or more additional therapies, including e.g., additional therapies directed at increasing the fertility of the subject. In some instances, a therapeutic regimen for enhancing the fertility of a subject may include administering platelet rich plasma to the subject. Such additional therapies directed at increasing the fertility of the subject will generally be administered after a period of the subject method where infertility is induced and, in some instances, may be administered during a holiday period, including e.g., during a holiday period from pharmacological agent administration, during a holiday period from physical regimen administration, during a holiday period from sleep regimen administration, during a holiday period from Eastern medicine administration, and the like.

Analysis and Monitoring

As summarized above, in some instances, the methods of the present disclosure may include analyzing a subject and/or monitoring a subject, including e.g., where such analyzing and/or monitoring is employed as part of a therapeutic regimen to enhance fertility. A subject may be analyzed or monitored to assess the subject's fertility (including assessing induced infertility), including before, during (i.e., concurrent), or following (including immediate-, short- or long-term follow-up) treatment. The fertility of a subject may be determined or measured by any convenient means including e.g., the ability of the subject to conceive upon regular attempts (i.e., normally productive intercourse), the ovulation frequency of the subject, measuring the levels of one or more fertility related hormones or other fertility biomarkers, one or more imaging based diagnostic methods (including e.g., ultrasound imaging of the reproductive system including the ovaries), analysis and/or counting of one or more ovarian structures or cell types observed or retrieved from the ovary of the subject (e.g., as part of an in vitro fertilization (IVF) procedure or other infertility intervention).

The effectiveness of one or more agents for enhancing fertility and/or inducing infertility in a subject and monitoring of a subject who receives one or more of the subject agents can readily be determined by a person skilled in the medical and clinical arts. One or any combination of diagnostic methods, including physical examination, medical history and performance of analytical tests and methods described herein and practiced in the art (e.g., medical imaging including e.g., ultrasound) may be employed.

In some instances, monitoring may be employed to modulate a subject's therapy. For example, in some instances, an analysis of a subject may be performed (e.g., an analysis of a subject's fertility, an analysis of a subject's infertility, etc.) and the treatment of the subject may be altered based on the outcome of the assessment. Such monitoring may be performed continuously of discontinuously (i.e., intermittently). As such, the frequency of monitoring may vary and may include e.g., semi-daily, daily, bi-daily, semi-weekly, weekly, bi-weekly, semi-monthly, monthly, bi-monthly, quarterly, semi-yearly, yearly, bi-yearly, etc. In some instances, the result of an assessment directed to measuring fertility and/or infertility of a subject may indicate whether treatment should be initiated, altered, or terminated.

Monitoring and/or analysis may be performed on the subject (i.e., in vivo) or may be performed on a sample collected from the subject (i.e., ex vivo). In some instances, subjects may be monitored or analyzed for ovarian follicles, oocytes or other ovarian cell or tissue types, including the presence or amount of ovarian progenitor cells in one or both ovaries of the subject. Such monitoring and/or analysis may be performed with or independent of treatment, including before, during (i.e., concurrent), or following (including immediate-, short- or long-term follow-up) treatment. In some instances, a subject may be assessed to determine if ovarian progenitor cells are present in the subject's ovary. In some instances, a subject may be assessed to determine the amount of ovarian progenitor cells present in the subject's ovary. In some instances, the result of an assessment directed to measuring or detecting ovarian progenitor cells in the ovary may indicate whether treatment should be initiated, altered, or terminated.

Various means of assessing progenitor cells present in the ovary of a subject may be employed, including e.g., detection of one or more progenitor cells markers or a cellular proliferation assessment. Useful cellular markers in assessing ovarian progenitor cells include but are not limited to e.g., a pluripotency marker, a stem cell marker, a reprogramming marker, a marker of DNA double-strand breaks, a marker of DNA repair, a marker of tumor suppression, a marker of senescence, a marker of oxidative damage, an marker of epigenetic modification, a marker of proliferation and combinations thereof.

In certain embodiments, marker detection and/or measurement of marker level is performed using flow cytometry. Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus. Fluorescence-activated cell sorting (FACS) is a specialized type of flow cytometry. FACS provides a method for sorting a heterogeneous mixture of biological cells into two or more containers, generally one cell at a time, based upon the specific light scattering and fluorescent characteristics of each cell. The flow cytometer and the FACS machine are useful scientific instruments as they provide fast, objective and quantitative recording of signals, e.g., fluorescent signals, and/or detection of cellular characteristics, e.g., size, granularity, viability, etc., from individual cells as well as physical separation of cells of particular interest. Fluorescent signals used in flow cytometry, for instance when quantifying and/or sorting cells by any marker present on or in the cell, typically are fluorescently-tagged antibody preparations or fluorescently-tagged ligands for binding to antibodies or other antigen-, epitope- or ligand-specific agent, such as with biotin/avidin binding systems or fluorescently-labeled and optionally addressable beads (e.g. microspheres or microbeads). The markers or combinations of markers detected by the optics and/or electronics of a flow cytometer vary and in some cases include but are not limited to: cell surface markers, intracellular and nuclear antigens, DNA, RNA, cell pigments, cell metabolites, protein modifications, transgenic proteins, enzymatic activity, apoptosis indicators, cell viability, cell oxidative state, etc.

In certain instances, flow cytometry is performed using a detection reagent, e.g., a fluorochrome-labeled antibody, e.g., a monoclonal antibody, with specific avidity against a cell surface maker of interest. A cellular sample is contacted with a detection reagent under conditions sufficient to allow the detection reagent to bind the cell surface maker and the cells of the sample are loaded into the flow cytometer, e.g., by first harvesting the cells from a cell culture using methods known in the art or described herein and re-suspending the isolated cells in a suitable buffer, e.g., running buffer. The cells loaded into the flow cytometer are run through the flow cytometer, e.g., by flowing cell containing buffer or liquid sample through the flow cell of the flow cytometer. The flow cytometer detects events as the cell passes one or more detection areas of the flow cytometer. For example, the flow cytometer may detect fluorescence emitted from a fluorochrome of a detection reagent upon excitation of the fluorochrome with a particular wavelength of light. In some instances, the flow cytometer detects the relative intensity of a particular signal, e.g., fluorescence of a particular detection reagent, of a particular cell, e.g., to quantify the level of a marker present on the surface of the cell and/or to qualitatively categorize the cell, e.g., as a cell that is positive for a particular marker or a cell that is negative for a particular marker. Detected events are counted or otherwise evaluated by the flow cytometer with or without input from an operator and used to determine, e.g., the total number of cells, the number or proportion of cells bound to a particular detection reagent, etc. In instances where FACS is utilized cells may be sorted, e.g., into separate containers, based on the detection or measurement of a particular marker. In some instances, cell sorting, e.g., by FACS, may be utilized to generate a purified population of a desired cell type.

In some instances, a threshold level of a particular detectable marker is used to categorize cells for sorting by FACS. Threshold levels may be used to categorize cells as "positive", "negative, "high", "low", etc. for a particular marker based on the level of detection of the marker. In some instances, a marker threshold level is determined by making a comparison of the levels of marker within a population of cells, e.g., a population of cells of unknown expression levels of Marker X or a population of cells suspected of containing subpopulations of cells having different expression levels of Marker X. For example, the expression level of Marker X is measured on a flow cytometer of at least a sufficient number of cells such that the measurements may be plotted, e.g., on a histogram, and separation between two or more subpopulations of cells is revealed based on individual cell expression levels of Marker X. Accordingly, the flow cytometer operator may then determine a threshold level between the subpopulations that may be used to categorize cells as belonging to a particular subpopulation, e.g., a subpopulation having a low level of expression of Marker X or a subpopulation having high level of expression of Marker X.

Expression markers of interest may be used to identify a particular cell type or verify that a derived cell type expresses a characteristic component of the derived cell type. In some instances, detection of expression markers may allow for optimization of a particular differentiation protocol, e.g., to optimize production of a desired cell type based on detection of one or more expression markers. Expression markers will vary depending on the type of cell to be identified or verified and/or desired downstream uses of the cell following identification or verification with the expression marker. Types of expression markers will include but are not limited to, e.g., gene expression marker, protein expression markers, expressed reporters, and the like. Expression marker detection and/or measurement may be detrimental to cell viability (e.g., wherein detection requires lysing or fixing a cell of interest) or may be essentially neutral to cell viability (e.g., wherein detection does not require lysing or fixing a cell of interest and may be performed on live cells).

Gene expression markers include but are not limited to the presence, absence, and/or relative amounts of a particular gene transcript that is indicative of particular cell type. Protein expression markers include but are not limited to the presence, absence, and/or relative amounts of a particular expression product that is indicative of particular cell type. Protein expression markers may be intercellular proteins, intracellular proteins or cell surface proteins. In some instances, a gene expression marker and a protein expression marker derived from the same gene may be indicative of a particular cell type.

Methods of detecting and/or measuring gene expression and/or protein expression are well-known in the art and include but are not limited to, e.g., Northern blot, Western blot, ELISA, PCR, quantitative PCR, in situ hybridization, fluorescent in situ hybridization, immunohistochemistry, immunofluorescence, microarray, quantitative sequencing, RNAseq, quantitative mass spectrometry, and the like.

Flow cytometric analysis methods may be employed at any convenient point in the subject methods, including e.g., analysis of cells collected from a subject (e.g., an ovary of a subject) prior to treatment, analysis of cells collected from a subject (e.g., an ovary of a subject) during to treatment, analysis of cells collected from a subject (e.g., an ovary of a subject) to detect a compensatory response to treatment, analysis of cells collected from a subject (e.g., an ovary of a subject) after to treatment, analysis of cells collected from a subject (e.g., an ovary of a subject) after a compensatory response to treatment, monitoring of the effectiveness of an ongoing treatment regimen, counting and/or other analysis of cells obtained from a treated subject, and the like.

The assessments and monitoring described herein may be combined with regular health assessments of a subject, including e.g., regular check-ups or diagnostic procedures, such as e.g., regular gynecological procedures. In some instances, the assessments and monitoring described herein may be performed independently from any regular health assessment of the subject.

Computer Readable Mediums and Programming Stored Thereon

The subject invention includes computer readable media having programming stored thereon for implementing the subject methods. For example, the subject invention may include suitable computing means such as suitable hardware/software for performing the subject methods.

In certain embodiments, programming may control a device to administer a pharmacological agent to a subject, e.g., programming may be configured to determine suitable dosage, etc. In certain embodiments programming may control a device to administer a sleep modulating stimulus to a subject, e.g., may control the activation/termination of sleep modulating stimulus including selecting suitable parameters. Programming may be configured to, or otherwise be capable of, directing a microprocessor to activate, i.e., turn "on" and "off" a device. For example, if so determined, the processor may direct the device to provide the appropriate pharmacological agent or stimulus to result in the desired action. Accordingly, a processor may select the appropriate parameters (e.g., frequency, dose, etc.) depending on what is required and direct a device to implement the parameters.

Programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means and process that information to determine if intervention is required. The result of that processing may be communicated to a user, e.g., via audio and/or visual means, e.g., the algorithm may also include steps or functions for generating a variety of profile graphs, plots, etc.

The subject invention may also include a data set of known or reference information stored on a computer readable medium to which data collected may be compared for use in determining a given treatment regimen. The data may be stored or configured in a variety of arrangements known to those of skill in the art.

Kits and Systems

Also provided are kits and systems for practicing the subject methods. Kits and systems may include devices (e.g., a drug delivery device, a regimen administering device, a sleep modulating device, an Eastern medicine delivery device, etc.), including those as described above. Devices which induce infertility in a subject, such as pharmacological delivery devices, physical activity modulating devices, sleep modulating devices, Eastern medicine delivery devices, and the like, may be referred to in the subject kits and systems an infertility producing components. In some instances, a subject device may represent an entire infertility producing component and in other instances, a component of a device or combination of components of a device may make up an infertility promoting component.

The subject kits and systems may further include devices for delivering, e.g., implanting, devices (e.g., implantable drug delivery devices) or components thereof (e.g., implantable sensors) to a target site of a subject such as into a body cavity of a subject may also be included in the subject kits. For example, an endoscope, introducer needle, and the like may be provided.

The subject kits and systems may also include one or more pharmacological agents, as described above. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit or system. The particular delivery means provided in a kit is dictated by the particular pharmacological agent employed, as described above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, intrauterine, intravaginal, etc. Accordingly, certain systems may include a suppository applicator, a vaginal applicator, a uterine applicator, syringe, I.V. bag and tubing, sensor, etc.

The subject kits and systems may also include instructions for how to practice the subject methods using the components of the kit or system. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits and systems may be packaged in suitable packaging to maintain sterility. In many embodiments of the subject kits and systems, the components of the kit are packaged in a kit containment element to make a single, easily handled unit, where the kit or system containment element, e.g., box or analogous structure, may or may not be an airtight container, e.g., to further preserve the sterility of some or all of the components of the kit or system.

Utility

The subject methods, systems and kits find use in enhancing fertility of a female subject, including, as reviewed above, female subject with normal or abnormal fertility. The methods of the present disclosure include enhancing the fertility of various subjects. In some instances, the treated subject is a healthy subject, i.e., a subject not suffering from any chronic or acute affliction, condition or disease, including but not limited to e.g., cancer and the like. The fertility of healthy subjects may be enhanced, e.g., to the normal level of fertility of a corresponding but younger subject, including a subject 5 years younger, 10 years younger, 15 years younger, 20 years younger, 25 years younger, etc. In some instances, fertility of a subject may be enhanced to a level higher than that of a normal healthy individual of corresponding age.

Infertility, as used herein, is generally not considered a disease and, as such, a treated subject may be a healthy subject with infertility. Such subjects may be treated, e.g., to at least reduce the infertility in the subject and improve the subject's fertility, including where the subject's fertility is increased to that of a normally fertile subject of corresponding age (i.e., below average fertility may be increased to correspond with expected average fertility of a subject of corresponding age and health). In some instances, the fertility of a subject with below average fertility may be increased to a level above that of a normally fertile subject of corresponding age.

As summarized above, infertility may be the consequence of one or more adverse health conditions or disease. As such, in some instances, the methods may include treating an unhealthy subject (i.e., a subject with a disease or adverse health condition) with infertility that is a result of a disease or adverse health condition of the subject. Such subjects may be treated, e.g., to at least reduce the infertility in the subject and improve the subject's fertility, including where the subject's fertility is increased to that of a normally fertile subject of corresponding age (i.e., below average fertility may be increased to correspond with expected average fertility of a subject of corresponding age and health). In some instances, in the fertility of a subject with below average fertility may be increased to a level above that of a normally fertile subject of corresponding age.

The fertility of a subject may be determined or measured by any convenient means including e.g., the ability of the subject to conceive upon regular attempts (i.e., normally productive intercourse), the ovulation frequency of the subject, measuring the levels of one or more fertility related hormones or other fertility biomarkers, one or more imaging based diagnostic methods (including e.g., ultrasound imaging of the reproductive system including the ovaries), analysis and/or counting of one or more ovarian structures or cell types observed or retrieved from the ovary of the subject (e.g., as part of an in vitro fertilization (IVF) procedure or other infertility intervention).

In some cases, the fertility of the subject may be increased to prolong fertility in the subject, including healthy and unhealthy subjects. Fertility may be prolonged beyond the average of menopause, including where the average of menopause is adjusted or calculated for a particular subject, e.g., as based on demographic, life history, family history, or other factors. Accordingly, in some instances, fertility may be prolonged 1 year or more beyond the average age of menopause onset, including e.g., 2 years or more, 3 years or more, 4 years or more, 5 years or more, 10 years or more, etc. Where a subject is expected to have premature or early menopause onset (e.g., based on particular life history, family history, or one or more risk factors) the method may increase fertility in the subject closer to a normal level, including e.g., closer to the average age of menopause onset, including e.g., within 10 years or less of the average age of menopause onset, e.g., within 5 years or less, within 4 years or less, within 3 years or less, within 2 years or less, within 1 year or less, etc. In some instances, fertility of a subject at risk of premature or early menopause may be prolonged to at least an average age of menopause onset or beyond.

As summarized above, the present disclosure includes methods of treatment for enhancing fertility, restoring fertility of an infertile subject, enhancing the duration of fertility in a subject at risk of premature or early menopause, etc. Such methods may include inducing infertility of a subject in a manner effective to cause the subject to mount a compensatory response, as described above.

A variety of subjects are treatable according to the herein described methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and non-human primates (e.g., humans, chimpanzees, and monkeys). In many embodiments, the subject may be human.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of enhancing reproductive capacity in a female subject, the method comprising:
    determining that the subject has decreased reproductive capacity; and inducing infertility in the subject in a manner effective to cause the subject to mount a compensatory response effective to enhance the reproductive capacity in the subject.

2. The method according to claim 1, wherein the inducing comprises administering a pharmacological agent to the subject.

3. The method according to claim 1, wherein the inducing comprises administering a physical regimen to the subject.

4. The method according to claim 1, wherein the inducing comprises administering a sleep regimen to the subject.

5. The method according to claim 1, wherein the inducing comprises administering an eastern medicine to the subject.

6. The method according to claim 5, wherein the eastern medicine comprises acupuncture, acupressure or a combination thereof.

7. The method according to claim 1, wherein the inducing is performed for a period of not less than 2 months.

8. The method according to claim 1, wherein the inducing is performed for a period of not more than 5 years.

9. The method according to claim 1, wherein the method further comprises evaluating the subject to determine the subject's reproductive capacity prior to the inducing.

10. The method according to claim 9, wherein the evaluating comprises administering a fertility test.

11. The method according to claim 9, wherein the evaluating comprises analyzing a prior attempt at conception.

12. The method according to claim 1, wherein the method further comprises monitoring the induced infertility in the subject.

13. The method according to claim 1, wherein the method further comprises evaluating the subject to determine the subject's reproductive capacity following the inducing.

14. The method according to claim 1, wherein the method comprises inducing infertility in the subject for a first period and monitoring the subject for a response thereto; and inducing infertility in the subject for a second period, wherein the second period is determined based on the monitored response to the first period.

15. The method according to claim 14, wherein the first period comprises administering a pharmacological agent to the subject.

16. The method according to claim 14, wherein the first period comprises administering a physical regimen to the subject.

* * * * *